United States Patent [19]

Neckers

[11] 4,416,826
[45] Nov. 22, 1983

[54] PERESTERS AND USE THEREOF

[76] Inventor: Douglas C. Neckers, Perrysburg, Ohio

[21] Appl. No.: 202,040

[22] Filed: Oct. 29, 1980

[51] Int. Cl.³ .............. C07D 265/30; C07D 211/60; C07D 307/20; C07C 179/18
[52] U.S. Cl. .............. 260/453 RZ; 544/106; 544/172; 544/153; 546/245; 546/225; 546/226; 546/196; 549/29; 549/72; 549/488; 549/60; 549/310
[58] Field of Search .............. 260/453 RZ; 544/106, 544/172; 546/245, 225, 226; 549/29, 72, 488

[56] References Cited

U.S. PATENT DOCUMENTS

| | | | |
|---|---|---|---|
| 2,456,198 | 9/1943 | Greenlee | 260/453 RZ |
| 2,484,487 | 10/1949 | Coldwell | 260/453 RZ |
| 2,575,440 | 11/1951 | Bradley | 260/453 RZ |
| 2,842,851 | 7/1958 | Dexter | 260/453 RZ |

OTHER PUBLICATIONS

Matsura et al., Tetrahedron, vol. 25, pp. 4487–4499, 1969.
Walling et al., JACS, vol 87, 7-5-65, No. 13, pp. 3413–3417.
Teffler et al., JACS, vol. 93, 1971, p. 7005–7012.
Thijs et al., J. Org. Chem., vol. 44, No. 23, 1979, p. 4123–4129.
Smith, JACS, vol. XLIII, 1921, (1920).
Friestone et al., J. Org. Chem., vol. 39, 11-15-74, Numbers 23, p. 3384.
Sammes, Tetrahedron, vol. 32, pp. 405–422, 1976.

Primary Examiner—Henry R. Jiles
Assistant Examiner—Robert C. Whittenbaugh
Attorney, Agent, or Firm—Harry Falber

[57] ABSTRACT

Peresters of the formula:

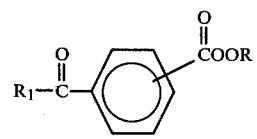

wherein R is an alkyl group; and

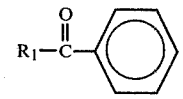

light-absorbing chromophore group; and use thereof as photoinitiators are provided.

10 Claims, No Drawings

PERESTERS AND USE THEREOF

DESCRIPTION

1. Technical Field

The present invention is based upon work supported by the National Science Foundation under NSF Grant DMR78-08493.

The present invention is concerned with new organic compounds which are particularly suitable as photoinitiators. The present invention is especially concerned with peresters. The peresters of the present invention are especially useful as photoinitiators for the polymerization of ethylenically unsaturated materials.

2. Background Art

Photoinitiators are free-radical sources which decompose photochemically and are employed especially as initiators in the polymerization of ethylenically unsaturated materials. In view of the efficient control photoinitiated polymerization offers, such has assumed great importance in recent years in the printing and electronics industries such as in printing inks, paints, and photoresist coatings.

Among typical commercial initiators are three general types: mixtures of aryl ketones, benzoin ethers, or substituted acetophenones. In past years, highly halogenated aryl hydrocarbons were also used for initiators, but their use is now precluded because they are so highly toxic.

Among the more important commercially used photoinitiators for acrylate polymerization is the so-called "Hammond initiator", benzophenone-Michler's ketone.

A major advantage of the Hammond initiator is the rate by which it initiates radical chain reactions; two important disadvantages are the rather large amount of initiator needed to make the rate of polymerization sufficiently rapid for printing applications and the potential toxicity of one of the initiator partners—Michler's ketone (4,4'-bis(N,N-dimethylamino)benzophenone).

To be of real practical significance as a photoinitiator, a compound must be relatively thermally stable but must also be labile when irradiated with wavelengths of UV or visible light. Accordingly, providing new compounds which possess this combination of properties is quite difficult. For instance, various benzophenone derivatives of benzoyl peroxide have been studied. For example, see Leffler et al; Journal American Chemical Society, 1971, 93, 7005 et seq. However, such derivatives are not especially stable thermally. It has also been noted that the photochemical efficiency of triplet benzophenone sensitized decompositions of peroxides in solution is low (e.g.—see Walling et al, Journal American Chemical Society, 1965, 87, 3413 et seq.).

SUMMARY OF INVENTION

An object of the present invention is to provide new compounds which have the requisite combination of relative thermal stability and efficient photodecomposability to be effective and practical photoinitiators.

The compounds of the present invention are peresters which contain a light absorbing chromophoric moiety. The compounds of the present invention exhibit thermal stability characteristics. However, the compounds of the present invention, unlike prior known peresters, are readily photodecomposable and effective photoinitiators for the polymerization of ethylenically unsaturated compounds. The present invention also makes it possible to control or tune the photodecomposition of the compounds by the absorption characteristics of the light-absorbing chromophore portion of the compound.

The compounds of the present invention are represented by the formula:

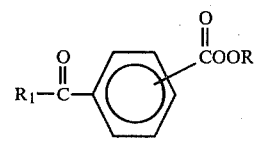

wherein R is an alkyl group; and

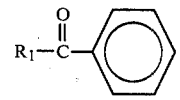

is a chromophore group.

The present invention is also concerned with photopolymerizable compositions comprising at least one photopolymerizable ethylenically unsaturated material and at least one of the above-discussed peresters.

Moreover, the present invention is concerned with polymerizing the above-defined photopolymerizable compositions by subjecting such to light, and polymer obtained thereby.

DESCRIPTION OF BEST AND VARIOUS MODES

The compounds of the present invention are represented by the formula:

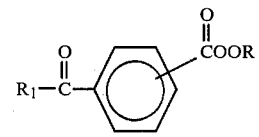

wherein R is an alkyl group; and $R_1$ is an organic or hydrocarbyl group such that the

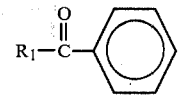

group is a chromophore group which produces an excited state by absorption preferably by n-$\pi$* absorption and which is free from nonbenzenoid unsaturation and/or polymeric moiety from nonbenzenoid unsaturated monomeric moiety. R is an alkyl group which generally contains 1 to 22 carbon atoms and preferably 1-12 carbon atoms which may be straight or branched chain. The preferred R groups preferably contain a tertiary carbon atom connected to the oxygen atoms for increased thermal stability. The most preferred R group is tert.-butyl.

Examples of some suitable $R_1$ groups are alkyl groups, cycloalkyl groups, aryl groups, substituted aryl groups, aralkyl groups; alkaryl groups; and heterocyclic groups. Generally the $R_1$ groups contain from 1 to 22 carbon atoms, and preferably 1-12 carbon atoms.

Examples of some alkyl groups are methyl, ethyl, t-butyl, t-amyl, hexyl, 2-ethylhexyl, nonyl and octodecyl.

Examples of some suitable aryl groups include phenyl, phenanthryl, and anthracyl.

Examples of some cycloalkyl radicals include cyclopropyl, cyclopentyl, cyclobutyl, cyclohexyl, cycloheptyl, cyclooctyl, and cyclododecyl.

Examples of some aralkyl groups are phenylmethyl and naphthylethyl.

Examples of some alkaryl groups include tolyl, xylyl and cumyl.

Examples of substituted aryl groups in addition to alkaryl include alkoxy-substituted aryl groups, such as methoxyphenol. The substituted aryl groups usually contains 1, 2 or 3 substitutions which are usually ortho and/or para with respect to the carbonyl group to which the substituted aryl group is connected.

The heterocyclic groups generally contain 5–6 members in the ring and contain S, O and/or N in the ring and include morpholinyl, piperidyl, thiophenyl, and furanyl.

The preferred $R_1$ groups are aryl and substituted aryl groups and the most preferred $R_1$ groups are phenyl and alkyl and/or alkoxy-substituted phenyl wherein the alkyl and/or alkoxy groups contain 1 to 22 carbon atoms and preferably 1–12 carbon atoms.

The two carbonyl groups located on the benzene rings can be ortho, meta, or, preferably, para to each other.

Some compounds of the present invention include

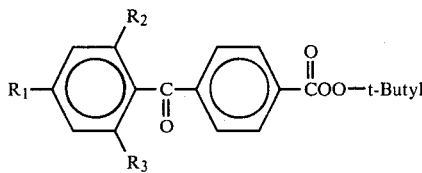

wherein
$R_1=R_2=R_3=H$
$R_1=R_2=R_3=CH_3$
$R_1=CH_3O; R_2=R_3=H$
$R_1=CH_3; R_2=R_3=H;$

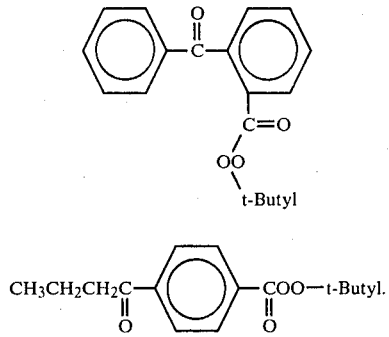

The compounds of the present invention can be readily obtained from the corresponding carboxylic acids. In particular, the corresponding carboxylic acid can be reacted at elevated temperature (e.g. up to about 60° C.), preferably at reflux, with, for example, thionyl chloride to form the corresponding acid chloride. Next, the acid chloride can be reacted with a hydroperoxide, such as tert.-butyl hydroperoxide in the case of R being t-butyl, usually in the presence of a tertiary amine, preferably triethylamine. In addition, it is preferred that this stage of the preparation be carried out in the presence of a diluent, such as ether, benzene, or dichloromethane.

The compounds of the present invention are especially useful as photoinitiators in the polymerization of photopolymerizable ethylenically unsaturated materials. The photopolymerizable materials can be monomeric or prepolymers containing one or more ethylenically unsaturated groups.

Examples of some suitable photopolymerizable materials include esters of unsaturated monocarboxylic acids or dicarboxylic acids, e.g. esters of acrylic acid, methacrylic acid, α-cyanacrylic acid, sorbic acid, fumaric acid or itaconic acid with aliphatic, cycloaliphatic or aromaticaliphatic monohydric to tetrahydric alcohols of 3 to 20 carbon atoms, e.g. methyl acrylate and methacrylate; n-, i- and t-butyl acrylate and methacrylate; 2-ethylhexyl acrylate; lauryl acrylate; dihydrodicyclopentadienyl acrylate and methacrylate; methylglycol acrylate; hydroxyethyl acrylate and methacrylate; hydroxypropyl acrylate and methacrylate; ethylene glycol diacrylate; diethylene glycol diacrylate; triethylene glycol diacrylate; neopentylglycol diacrylate and dimethacrylate; 1,4-dimethylolcyclohexane diacrylate; pentaerythritol-triacrylate, -tetraacrylate, -trimethacrylate and -tetramethacrylate; ethyl α-cyanacrylate; ethyl crotonate, ethyl sorbate; diethyl fumarate; and the diacrylate and dimethacrylate or oxyalkylated bisphenol A; amides of acrylic acid or methacrylic acid which may or may not be substituted at the nitrogen by alkyl, alkoxyalkyl or hydroxyalkyl, e.g., N,N'-di-methylacrylamide, N-isobutylacrylamide, diacetoneacrylamide; N-methylolacrylamide, N-methoxymethylacrylamide, N-butoxymethylacrylamide, N-butoxymethylmethacrylamide and ethylene glycol bis(N-methylolacrylamide)ether; vinyl esters of monocarboxylic acids or dicarboxylic acids of 2 to 20 carbon atoms, e.g., vinyl acetate, vinyl propionate, vinyl 2-ethylhexanoate, vinyl versatate and divinyl adipate; vinyl ethers of monohydric or dihydric alcohols of 3 to 20 carbon atoms, e.g., isobutyl vinyl ether, hexyl vinyl ether, octadecyl vinyl ether, ethylene glycol divinyl ether, diethylene glycol divinyl ether, butanediol divinyl ether and hexanediol divinyl ether; mono-N-vinyl compounds, e.g., N-vinylpyrrolidone, N-vinylpiperidone, N-vinylcaprolactam, N-vinylmorpholine, N-vinyloxazolidone, N-vinylsuccinimide, N-methyl-N-vinylformamide and N-vinylcarbazole; allyl ethers and allyl esters, e.g., trimethylolpropane diallyl ether, trimethylolpropane triallyl ether, pentaerythritol triallyl ether, diallyl maleate, diallyl fumarate or diallyl phthalate; vinyl and vinylidine halides, e.g., vinyl chloride and vinylidene chloride; and vinyl aromatics, e.g., styrene, alkyl styrenes, halostyrenes and divinylbenzenes.

Examples of some polymeric photopolymerizable materials include unsaturated polyesters obtained, for instance, from α,β-unsaturated dicarboxylic acids, e.g., maleic acid, fumaric acid or itaconic acid, and aliphatic, cycloaliphatic or non-phenolic aromatic diols, e.g., ethylene glycol, diethylene glycol, triethylene glycol, propane-1,2-diol, propane-1,3-diol, butane-1,2-diol, butane-1,3-diol, butane-1,4-diol, but-2-ene, 1,4-diol, neopentylglycol, hexane-1,6-diol or oxyalkylated bisphenol A; unsaturated epoxide-acrylates obtained, for instance, from monofunctional epoxides and acrylic acid or methacrylic acid, by the method of U.S. Pat. No.

2,484,487, bifunctional epoxides and unsaturated fatty acids, by the method of U.S. Pat. No. 2,456,408, polyfunctional aromatic epoxides and crotonic acid, by the method of U.S. Pat. No. 2,575,440 or polyfunctional aromatic or aliphatic fatty glycidyl ethers and acrylic acid or methacrylic acid, by the method of U.S. Pat. No. 2,842,851; unsaturated polyurethanes (urethane-acrylates) prepared from hydroxyalkyl acrylates and diisocyanates, with or without polyols or polyamines; unsaturated copolymers, prepared, for example, by reacting copolymers, containing maleic anhydride groups, with unsaturated alcohols; or acrylic ester copolymers containing carboxylic acid groups or polyesters containing carboxylic acid groups with unsaturated epoxides, e.g., glycidyl acrylates; butadiene polymers in which the double bonds are predominantly present as vinyl side chains; diallyl phthalate prepolymers; and poly-N-vinylurethanes, e.g. prepared, for instance, by reacting vinyl isocyanate with saturated or unsaturated polyesterpolyols, polyether-polyols or polyfunctional alcohols.

The peresters when employed as photoinitiators are usually present in amounts of about 1 to about 10%, and more usually about 1 to about 3% by weight based upon the weight of the photopolymerizable material present. The polymerization of such compositions can be carried out by subjecting or exposing the compositions to light (e.g., UV or visible) of appropriate wavelength absorbable by the chromophore moiety of the perester employed. The compounds of the present invention can be tailored by the particular chromophore group present to provide light absorption properties for a given wavelength selected from a broad spectrum of wavelengths, preferably in the visible and UV ranges. It is preferred that the chromophore group be selected so that it absorbs light in the range of about 250–700 nm. The particular wavelength to employ is determinable by those skilled in the art without undue experimentation once they are aware of the present invention and the particular chromophore group present.

Polymers obtained from polymerization in the presence of the peresters of the present invention have been found to contain as end group the chromophore group from the perester employed; and, therefore, can subsequently be subjected to irradiation to achieve some crosslinking. For instance, polystyrene obtained from irradiating styrene in the presence of t-butyl-4-benzoylperbenzoate contains one benzophenone end group, and is, therefore, crosslinkable at 366 nm.

Polymerization of the composition usually requires exposure to the light for about 30 seconds to about 10 minutes depending upon the amount of initiator present. The time and amount are inversely related. The crosslinking reaction is usually about $10^2$ to $10^3$ times slower than the polymerization and usually requires about 1 to about 20 hours depending upon the amount of initiator employed.

The following non-limiting examples are presented to further illustrate the present invention:

EXAMPLE 1

Preparation of Peresters a. Preparation of t-Butyl-4-Benzoylperbenzoate

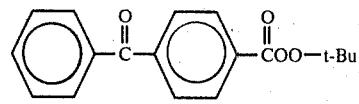

About 1 part of p-benzoylbenzoic acid is admixed with about 5 parts of thionyl chloride and a few drops of pyridine, and the mixture is heated to boiling (about 78° C.) and maintained under reflux conditions until the production of HCl ceases. The resulting acid chloride is purified by crystallization from cyclohexane.

About 10 mmol of the acid chloride are dissolved in about 50 mL of ether. The solution is stirred magnetically and cooled in an ice-water bath while a solution of about 11 mmol of tert-butyl hydroperoxide and about 12 mmol of triethylamine in about 20 mL of ether is added over a period of about 5 minutes. After the addition is completed, the reaction mixture is stirred for another hour at ice-water bath temperatures. The desired perester, t-butyl-4-benzoylperbenzoate is obtained by filtration and evaporation. In addition, the perester is purified by chromatography over silica gel having a mesh of about 60 to about 200 using $CH_2Cl_2$ as eluent and then recrystallization from an ether-pentane mixture.

Melting points of the peresters are determined on a Thomas-Hoover capillary melting point apparatus and are uncorrected. Infrared spectra are recorded in KBr disks or neat, using a Perkin-Elmer 337 infrared spectrophotometer (when other conditions are used they are given at the appropriate place). NMR spectra are recorded either on a Varian A-60 or CFT-20 spectrometer with deuteriochloroform as the solvent and tetramethylsilane as the internal reference.

UV spectra are determined using a Beckman Acta MIV spectrophotometer. Mass spectra are obtained using a Varian MAT Model CH-7 mass spectrometer. GLC measurements are made on a Hewlett Packard 5710 A TD or 5710 FID chromatograph. High-pressure LC chromatograms are run on a Waters Associates instrument with UV detection and a Porasil column.

b. Preparation of t-Butyl-4-(4'-Methylbenzoyl)perbenzoate

Tert-butyl-4-(4'-methylbenzoyl)perbenzoate is prepared by the above-discussed procedure for the preparation of t-butyl-4-benzoylperbenzoate, except that the starting acid employed is 4-(4'-methylbenzoyl) benzoic acid which is prepared by the Friedel-Crafts reaction of 4-(carbomethoxy)benzoyl chloride with toluene followed by saponification and acidification as suggested in Smith, Journal of American Chemical Society, 1921, 43, 1920, and Firestone et al, Journal Organic Chemistry, 1974, 39, 3384.

c. Preparation of t-Butyl-4-(2',4,',6'-Trimethylbenzoyl) Benzoic Acid

Tert-butyl-4-(2',4',6'-trimethylbenzoyl)perbenzoate is prepared by a method similar to that for the preparation of tert-butyl-4-benzoylperbenzoate except that the starting acid employed is 4-(2',4',6'-trimethylbenzoyl) benzoic acid which is obtained by the Friedel-Crafts reaction of 4-(carbomethoxy)benzoyl chloride with mesitylene followed by saponification and acidification as suggested by Benjamins et al, Journal of Chemistry, 1974, 52, 597, and Firestone et al, Journal of Organic Chemistry, supra.

d. Preparation of t-Butyl-4-(4'-Methoxybenzoyl)perbenzoate

Tert-butyl-4-(4'-methoxybenzoyl)perbenzoate is prepared by the above discussed procedure for the preparation of t-butyl-4-benzoylperbenzoate, except that the acid employed is 4-(4'-methoxybenzoyl)-benzoic acid, and during the preparation, the corresponding acid chloride is dissolved in a mixture of ether and dichloromethane.

The oil is subjected to chromographic treatment over silica gel using $CH_2Cl_2$ as eluent. About 4.5 grams of an oil is obtained which gives a solid on trituration with ether. The solid appears to be the below-defined psueodoperester which, in turn, is crystallized from dichloromethane-ether, giving a colorless compound having an mp of about 126° to about 128° C.; a $IR_{\nu_{C=O}}$ 1790 $cm^{-1}$ (no $C=O$ of benzoyl group); NMR 1.23 (s, 9H, $CH_3$), 7.2–8.7 (m, 9H, aromatic protons).

The oil is again subjected to chromatography and freed from psuedoperester by dissolving it in ether-pentane mixtures, cooling and then filtering.

The following Table I gives the various physical properties of the peresters in Examples 1a to 1f.

TABLE I

Physical Properties of the Peresters t-butyl-2-benzoyl perbenzoate pseudo-perester

| perester | | yield, % | mp, °C. | $\nu_{C=O}$ (ketone) | $\nu_{C=O}$ (adjacent to perester) | UV n − π*, nm | triplet energy $E_T$, kcal/mol |
|---|---|---|---|---|---|---|---|
| Ia | | 75 | 62–64 | 1665 | 1770 | 347 | 67.7 |
| Ib | | 70 | 75–77 | 1665 | 1770 | 349 | 67.4 |
| Ic | | 63 | 93–95 | 1665 | 1770 | 325 | |
| Id | | 78 | 80–81 | 1665 | 1770 | | |
| If | pseudoperester | mixture | oil | 1680 | 1175(neat) | 327 | |
| | perester | | 126–128 | | 1790(KBr) | none > 300 | |
| Ie | Ie | 52 | oil | 1700 | 1775(neat) | tail > 300 | |

IR absorption, $cm^{-1}$, in $CCl_4$ methane.

e. Preparation of tert-Butyl-p-Butyrylperbenzoate

Tert-butyl-p-butyrylperbenzoate is prepared by the above-discussed procedure for the preparation of t-butyl-4-benzoylperbenzoate, except that the acid employed is p-butyryl benzoic acid and is purified by chromatography over neutral aluminum oxide with dichloromethane-ether (5:1) as eluent. The perester obtained is a yellow oil which solidifies after several months in the refrigerator.

f. Preparation of Mixtures of tert-Butyl-2-Benzoylperbenzoate and Its Corresponding Pseudoester About 22 mmol of o-benzoylbenzoic acid is admixed with about 10 mL of thionyl chloride and heated to reflux for about 4 hours. The thionyl chloride is evaporated and the product obtained is a pseudoacid chloride which is an oil. The oil obtained is then dissolved in about 100 mL of ether and the solution cooled in an ice-salt bath. Over a period of about 15 minutes, a solution of about 23 mmol of t-butyl hydroperoxide and about 24 mmol of triethylamine in 25 mL of ether are added. A yellow color develops upon the addition of the first drops. Stirring is continued for about another hour after the addition is completed. Filtration and evaporation of the reaction mixture gives a yellow oil.

EXAMPLE 2

Decomposition of Peresters By Irradiation and Kinetics Thereof

The peresters are dissolved in concentrations as given in Table II. The amount of perester used is in the range of 300–500 mg. The solutions are placed in Pyrex tubes, flushed with nitrogen for 10 min., and sealed with a rubber cap.

After the irradiation, the yield of $CO_2$ is measured by applying $N_2$ pressure and trapping the $CO_2$ with a Ba(OH)$_2$ solution. The photolyzed solutions are evaporated (in the case of perester Ia treatment with excess diazomethane gives the best separation procedure) and again evaporated. Chromatography over 2 mm silica gel plates (E. Merck) with dichloromethane as the developing solvent separates the products. Extraction of the silica gel is done with ether. The identity of each sample is confirmed by GLC or high-pressure LC by comparison with authentic samples or by melting points of the solids.

All the peresters photodecompose with nearly unit quantum efficiency in both polar and nonpolar solvents when irradiated at the wavelength of carbonyl group absorption. In general, the photodecompositions occur as shown in Scheme I below.

The main products from the benzophenone moiety are the parent aryl ketone and the appropriate benzoic acid, though secondary photoproducts such as pinacols and other solvent-derived products are also formed, the quantity depending on the nature of the solvent. The main products and reaction conditions of the photolysis experiments for some peresters of Example 1 are given in Table II.

The decomposition of most of the peresters is faster in methanol than in cyclohexane. In the case of the mesitoyl perester, Ib, the effect of methanol is to slow the rate of decomposition.

The decarboxylation step of each perester derived carboxyl radical is not affected much by the solvent, but pinacol products are more prominent in methanol.

The irradiation of the butyrophenone perester, Ie, shows no evidence for a competing Norrish type II reaction. Thus, there is no acetophenone, no $p$-acetylbenzoic acid, and no $p$-acetyl tert-butylperbenzoate observed among the products from Ie. On the other hand, the formation of about 25% of the methyl ester of the expected acid as a photoproduct is somewhat difficult to explain but may come from a solvent-induced decomposition.

Concerning the byproducts formed, irradiation Ia in cyclohexane gives bicyclohexyl as a secondary photolysis product. This is shown by comparison with an authentic sample and combination of spectroscopic techniques. GLC indicates that minor fractions of $C_6H_5-CO-p-C_6H_4COO-c-C_6H_{11}$ are present in cyclohexane while in $CH_3OH$ a secondary photoproduct is $C_6H_5CHOH-p-C_6H_4COOH$. The same product is formed when 4-benzoylbenzoic acid is irradiated for 2 hours in $CH_3OH$ in 26% yield. The structure of this secondary photoproduct is shown by independent synthesis (reduction of methyl 4-benzoylbenzoate by $NaBH_4$). Among other secondary photoproducts found in small amounts is a mixture of pinacols. These are confirmed by synthesis of a similar pinacol mixture upon irradiation of methyl 4-benzoylbenzoate in isopropyl alcohol.

After photolysis of tert-butyl-4-(2',4',6'-trimethylbenzoyl)perbenzoate (Ic) (300 mg in 20 mL of $CH_3OH$) for 1 hour, the following products are found: 14.1% of $CO_2$, 15.6% of phenyl mesityl ketone, 56.6% of starting perester, and 21.8% of the corresponding acid.

The phenyl mesityl ketone shows no deuterium incorporation (mass spectrometry). The perester shows no deuterium incorporation (NMR).

The recovered perester is irradiated again in cyclohexane solution (25 mL) for 4 hours. The following products are found: carbon dioxide, 44%; bicyclohexyl (21 mg); mesityl phenyl ketone (52%); and the corresponding acid, 46%. No deuterium incorporation in the mesityl phenyl ketone is found.

After photolysis of tert-butyl-$p$-butyrylperbenzoate (Ie) (1 mmol in 30 mL of $CH_3OH$) for about 85 minutes, the following products are found: carbon dioxide, 11%; butyrophenone, 10% (confirmed by high-pressure LC): methyl $p$-butyrylbenzoate (25%) (mp 83°–85° C. from hexane) confirmed by independent synthesis); and $p$-butyrylbenzoic acid (52%) (confirmed by preparation of the methyl ester). No products of a Norrish type II reaction are found.

Kinetic studies are carried out in degassed, sealed tubes by irradiating them with 366 nm light obtained from a Hanovia medium-pressure mercury lamp by combining the Corning Filters 0–52 and 7–60. The decompositions of the peresters are followed by the carbonyl IR absorption adjacent to the peroxide group (O=COO—) (1770 cm$^{-1}$). Benzophenone-benzhydrol redox actinometry are used throughout the study. In particular, a solution of perester (2 mL) in the appropriate solvent is placed in Pyrex tubes (12-mm diameter), degassed, and sealed under vacuum. Three cycles of freeze-thaw removes dissolved oxygen. The tubes are placed in a merry-go-round around a water-cooled light source, removed at different predetermined intervals, and kept frozen in liquid nitrogen in the dark until analysis is done. The estimation of perester is done by quantitative IR, monitoring the carbonyl peak at 1770 cm$^{-1}$. None of the products of decomposition or the solvent interfere at this wavelength. Absorbance is measured with a 0.1 mm NaCl cell against solvent reference. With every run, two tubes containing actinometric solutions (benzophenone (0.1 M) and benzhydrol (0.05 M) in benzene are irradiated. The light intensity and quantum yield of benzophenone loss are measured by measuring the decrease in benzophenone content spectrophotometrically (using the benzophenone peak at 345 nm).

Quantum yields of decomposition of the peresters are shown in Table III below and are observed to be near unity in contrast to the low quantum yields of benzophenone-sensitized decomposition of $Bz_2O_2$ as discussed in Walling et al, American Chemical Society, 1965, 87, 3413.

The decomposition rates of the peresters show first-order reaction kinetics with little or no induced decomposition in benzene solution in the concentration range 0.04 to 0.07 M. The apparent first-order photodecomposition rate constants ($k_d$) (up to 40% conversion) in $C_6H_6$ are shown in Table IV below.

In methanol the quantum yield is much higher than in cyclohexane and higher than unity, suggesting the possibility of a solvent-induced decomposition.

To test this possibility, a radical scavenger 2,6-di-tert-butyl-$p$-cresol (TBP) is included in the reaction mixture; under these conditions the quantum yield in $CH_3OH$ reduces in value to that found in benzene. The rate of decomposition in benzene does not alter with addition of TBP, and the quantum yields, both in the presence and the absence of TBP, in methanol and $CCl_4$ are shown in Table V below. Thus, under conditions where the solvent-induced decomposition is eliminated by the radical scavenger, the quantum yield is the same in methanol as in nonpolar solvents.

All the peresters give linear Stern-Volmer plots when naphthalene is used as triplet quencher. The values of the slopes ($k_q\tau$) (Table VI below) suggest that the triplet lifetimes of the peresters are short when compared to those of benzophenone alone.

To test the thermal stability of the perester, attempts are made to measure decomposition rates at 80° C. in benzene. While $Bz_2O_2$ shows a decomposition rate comparable to the literature value, the peresters do not decompose at all at 80° C. The thermal rates of decomposition in the dark are measured at 110° C. in chlorobenzene (Table VII below) and are comparable in value to the rates of decomposition of substituted tert-butyl perbenzoates.

TABLE II

The Products of Photolysis from Different Peresters[e]

| perester | solvent | concn, M × 10² | period of irradiation, h | unreacted perester | benzoyl-benzoic acid | benzophenone |
|---|---|---|---|---|---|---|
| Ia | cyclohexane | 2.4 | 6 | 0 | 55 | 36[a] |
|    | methanol | 2.4 | 1 | 0 | 60 | 29[b] |
| Ib | cyclohexane | 2.0 | 2.5 | 29 | 27 | 20 |
|    |             | 2.2 | 4 | 0 | 46 | 43 |
|    | methanol | 4.2 | 1 | 61 | 13 | 19 |
|    | CH₃OH[d] | 4.4 | 1 | 57 | 21 | 16 |
| Ie | methanol | 3.3 | 1.5 | 0 | 52[c] | 10[c] |

[a]Minor byproducts are bicyclohexyl and $C_6H_5CO-p-C_6H_4COO-c-C_6H_{11}$.
[b]Further irradiation gives pinacols and $C_6H_5CHOH-p-C_6H_4COOH$.
[c]In addition to the acid, 25% methyl ester of the acid is also found.
[d]Decomposition of Ib in CH₂OH produces no deuterated mesitoyl phenyl ketone nor is there any deuterium in the recovered Ib.
[e]Irradiation light source 300 nm; Pyrex reactors purge with nitrogen.

TABLE III

Quantum Yields of Perester Decomposition and Sensitized Decomposition of Benzoyl Peroxide

| perester | concn, M × 10² | solvent | benzophenone concn, M × 10² | φ of dec |
|---|---|---|---|---|
| Ia | 5.90 | C₆H₆ |  | 0.94 |
| Ib | 6.06 | C₆H₆ |  | 0.80 |
| Ic | 5.03 | C₆H₆ |  | 0.75 |
| Bz₂O₂ | 4.67 | C₆H₆ | 5.89 | 0.32 |
| Bz₂O₂ | 3.50 | CCl₄ | 3.75 | 0.17 |

TABLE IV

Decomposition Rates of the Peresters and Sensitized Benzoyl Peroxide[a]

| perester | initial concn, M × 10² | benzophenone concn, M × 10² | $k_d × 10^4 \text{ s}^{-1}$ |
|---|---|---|---|
| Ia | 5.9 |  | 1.84 |
| Ib | 6.06 |  | 1.34 |
| Ic | 5.03 |  | 1.45 |
| Bz₂O₂ | 4.67 | 5.89 | 0.64 |

[a]Light intensity, I = 6.56 × 10¹⁷ quanta/min; solvent, C₆H₆; temperature 25° C.

TABLE V

Quantum Yields of the Peresters in Methanol and CCl₄[a]

| perester | concn, M × 10² | TBP concn, M × 10² | solvent | φ of dec |
|---|---|---|---|---|
| Ia | 7.16 |  | CCl₄ | 1.05 |
|    | 4.78 | 5.01 | CCl₄ | 0.79 |
|    | 3.56 |  | CCl₄ | 0.90 |
|    | 3.56 | 3.76 | CCl₄ | 0.74 |
|    | 5.38 |  | methanol | 2.77 |
|    | 5.38 | 5.08 | methanol | 0.64 |
| Ib | 6.15 |  | methanol | 1.30 |
|    | 6.15 | 5.08 | methanol | 0.62 |
| Ic | 5.10 |  | methanol | 1.54 |

[a]Radical-induced decomposition of Ia is greater than that of Ic and Ib.

TABLE VI

Quenching Constants for the Peresters

| peresters | quencher | solvent | $k_q\tau$ |
|---|---|---|---|
| Ia | naphthalene | CCl₄ | 7.5 |
| Ib | naphthalene | C₆H₆ | 15 |
| Ic | naphthalene | CCl₄ | 15 |

TABLE VII

Thermal Decomposition of the Peresters

| perester | initial concn, M × 10² | 1st order dec rate M × 10⁵ s⁻¹ | half-life, $t_{\frac{1}{2}}$, h |
|---|---|---|---|
| Ia | 5.01 | 2.88 | 6.7 |
| Ib | 5.15 | 1.80 | 10.7 |
| Ic | 5.19 | 3.03 | 6.4 |

The peresters all provide efficient photochemical sources of free radicals. Important from a practical view is that their photodecomposition is controllable (effectively it can be tuned) by the absorption characteristics of the absorbing chromophore. Thus p-benzoyl tert-butylperbenzoate decomposes smoothly at room temperature with 366 nm radiation. At this wavelength benzoyl peroxide is photostable. In hydrocarbon solvents where the likelihood of solvent-induced decomposition is minimized, the decomposition quantum yield approaches unity (Table III). The quantum efficiency of photodecomposition of the aroyl tert-butylperbenzoates is at least three times that of the benzophenone-sensitized decomposition of benzoyl peroxide, clearly indicating the efficacy of the intramolecular process in contrast to bimolecular energy transfer. In fact, all of the peresters tested decompose with higher quantum yields (by at least a factor of 3) than does benzoyl peroxide in the presence of benzophenone (Table III). The decomposition rates are also 2-3 times higher compared to benzophenone-sensitized benzoyl peroxide decomposition (Table IV). In methanol all of the perester decomposition quantum yields are enhanced, the result of induced decompositions which are chain reactions (Table V).

The potential for an intramolecular reaction in the mesitoyl perester (Ib) is suggested by its apparently slower rate of decomposition in methanol than either that of Ia or Ic under identical conditions. This suggests an intramolecular hydrogen abstraction leading to a photoenol, the latter being stabilized by the alcohol solvent. o-Alkylbenzophenones give photoenols when the n-π* triplet state abstracts hydrogen from the ortho substituent (see Tammes, Tetrahedron 1976, 32, 405). Though this process is reported to be inefficient for mesitoyl aryl ketones by Matsuura et al, Tetrahedron, 1969, 25, 4487, because the excited state is disrupted from planarity by the excessive o-methyls, there is reason to believe the latter theory is based on incomplete experimental evidence as discussed by Neckers, PhD Thesis, University of Kansas, 1963.

Photoenolization in the mesitoyl perester (Ib) would be indicated by deuterium incorporation if the reverse reaction is slow compared with intermolecular exchange (Scheme II). Only if the exchange with solvent is slow compared to reversion (a reaction expected to have a rate constant comparable to that of the reverse Norrish type II reaction in t-BuOH) would no deuterium incorporation be observed in the starting material recovered or in the products.

The experiments (Table II) indicate that no deuterium incorporation is observed either in the starting perester Ib or the products. This result suggests that photochemical perester decomposition from Ib is faster than is the intramolecular hydrogen abstraction from the methyl groups.

The result with the butyrophenone perester Ia is similar in that it too indicates that photolytic perester decomposition proceeds much more rapidly than formation of acetophenone derivatives which would be expected from a competitive Norrish type II reaction. The latter reaction is one in which abstraction from the alkyl chain would have to occur more rapidly than perester bond homolysis. This process would be indicated by acetyl products—either in the form of acetophenone, p-acetylbenzoic acid, or even perhaps p-acetyl tert-butylperbenzoate (Scheme III). None of these are observed.

The point is that few of the typical photochemical reactions of aryl ketones seem to compete with light absorption and perester decomposition—in that order in the case of the UV active peresters. None of the typical n-π* triplet ketone reactions of the aryl ketone systems tested are viable in competition with the homolysis of the —O—O— bond of the perester unit.

Scheme I

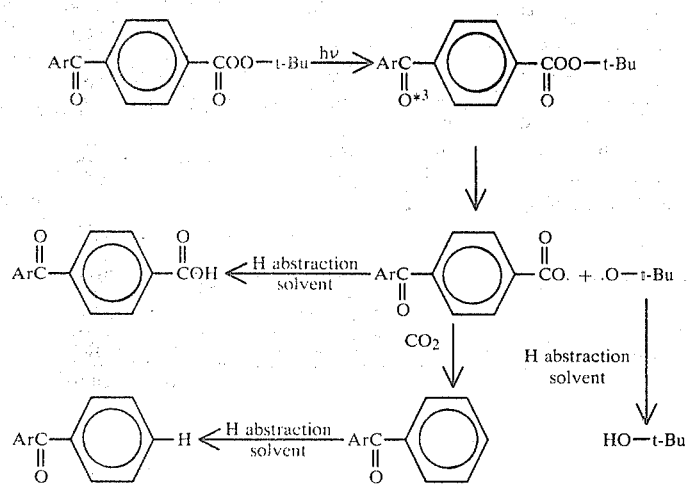

Scheme II

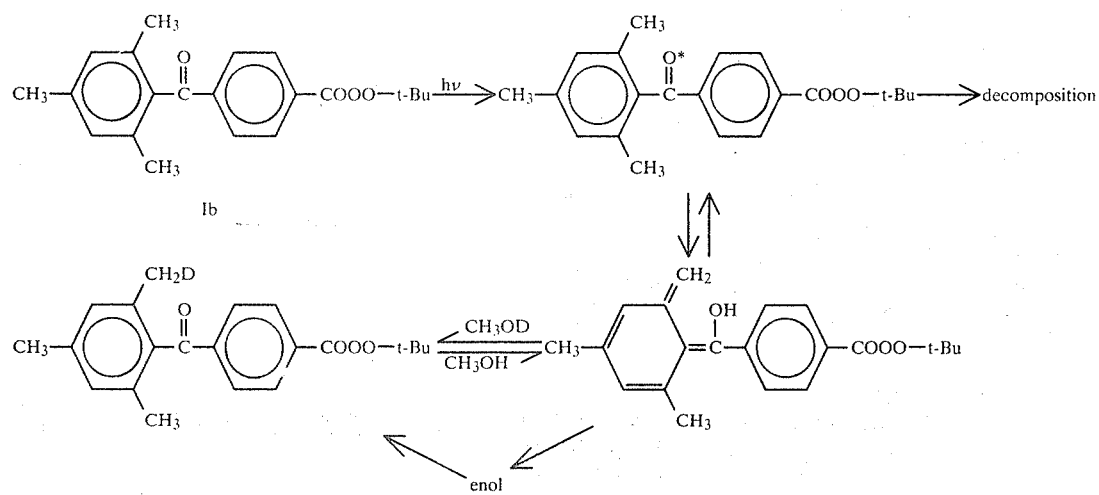

Scheme III

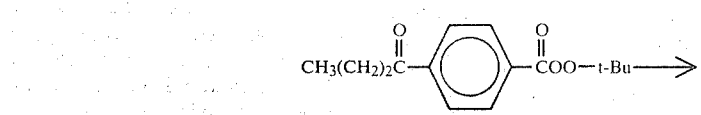

-continued

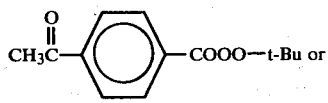

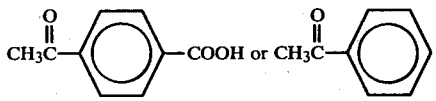

EXAMPLE 3

Use in Polymerization of Polyester 0.2 parts by weight of the photoinitiators of the present invention are incorporated in 10 parts Crystik-PKE 305 (Unsaturated polyester resin from Messr. Maeder, Switzerland). This mixture is stirred until a solution is obtained, which is then drawn out on glass plates with a film drawer (100μ). These films are irradiated with a medium-pressure Hg burner (Hanovia-Gerät, Model 45080). The samples are passed, on a conveyer belt, under the UV-lamp at a rate of 17 m/min. (20 volts).

The following Table gives the number of passes (P) which are necessary in order to obtain, with the photoinitiators according to the invention, films resistant to wiping. In addition, the hardness of the film is determined using a pendulum apparatus according to König.

same as that in the decomposition rate example hereinabove.

The results are shown in Table VIII below. The peresters of the present invention are each more efficient than is benzophenone-sensitized initiation using benzoyl peroxide or when benzophenone alone is used as an initiator. They are also comparable to the Hammond initiator in rate and have several advantages—by design. The thermal decompositions of the synthesized peresters are slow. In a thermal reaction, these peresters are quite similar to tert-butylperbenzoates.

Under the photolytic conditions employed, methyl methacrylate does not polymerize photochemically in the absence of any initiator.

TABLE VIII

| | Rate of Polymerization ($R_p$) of MMA[a] | |
|---|---|---|
| initiator | benzophenone concn, M × $10^2$ | $R_p × 10^5$ mL$^{-1}$ s$^{-1}$ |

| Photoinitiator | Passes necessary to achieve resistance to wiping | Pendulum hardness according to Konig, H, as a function of the number of passes P, H (P) | |
|---|---|---|---|
| 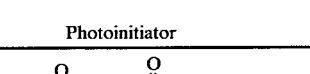 H$_3$CO—⟨⟩—C(O)—⟨⟩—C(O)—O—O—butyl | 14 | 23 (14) | 26 (16) |
| 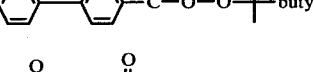 ⟨⟩—C(O)—⟨⟩—C(O)—O—O—butyl | 14 | 22 (14) | 26 (16) |
| 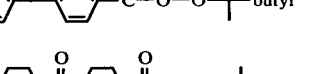 CH$_3$—⟨⟩—C(O)—⟨⟩—C(O)—O—O—butyl | 13 | 23 (13) | 51 (15) |
|  ⟨⟩—C(O)—⟨⟩—C(O)—O—O—butyl | 12 | 24 (12) | 38 (14) |
| Benzophenone (Comparison example) | >20 | wet | |

The rate of polymerization is much higher with the peresters than with benzophenone.

EXAMPLE 4

Use in Polymerization of Methyl Methacrylate

Commercial methyl methacrylate monomer is washed three times with 2% NaOH solution to remove stabilizer. It is then washed with distilled water three times, dried with molecular sieves, and distilled under vacuum before use. Polymerization solutions are prepared in cylindrical tubes which are degassed and sealed. The amount of polymer formed is determined by precipitating the polymer with an excess of methanol, washing with methanol, and filtering through fine sintered crucibles (previously weighed) followed by drying in a vacuum oven. The irradiation condition is the

| | | |
|---|---|---|
| Ia | | 8.33 |
| Ib | | 8.31 |
| Ic | | 8.16 |
| Bz$_2$O$_2$ | 5.5 | 2.58 |

[a]Initiator = 5 × $10^{-2}$ M, [MMA] = 3.1 M; temperature = 25° C., benzene.

EXAMPLE 5

Polymerization of Styrene

Commercial styrene is washed three times with ice cold 2% NaOH solution followed by washing (four times) with distilled water. The styrene is dried over anhydrous CaCl$_2$ and distilled under vacuum before use. The middle fraction of the distillate is used for polymerization. Solvents are purified by conventional means and distilled under $N_2$ atmosphere.

The irradiations are carried out in degassed (three cycles of freeze-thaw under high vacuum) sealed 15-mm Pyrex tubes. The tubes are placed in a merry-go-round with a filtered UV source of 366 nm at the center and the yield of polymer is measured (below 10% conversion) gravimetrically. In all of the cases, tubes of the same size and same volume of solution are used. Number-average molecular weights of the purified polymers are determined by viscometry in a benzene solution. After the polymerization, an aliquot of 0.5 ml from each reaction tube is placed in 2-ml volumetric flasks. The solvent and excess monomer are evaporated under high vacuum for several hours. The remaining flask contents are dissolved in 0.5 ml of benzene or chloroform and the polymer is precipitated by adding 0.5 ml of n-hexane. The solution then is centrifuged and the IR of the centrifugate is measured to determine undecomposed perester. All of the above procedures are carried out as far as possible in the dark. The light intensity is measured by benzophenone-benzhydrol actinometry and observed to be $I_o = 6.56 \times 10^{17}$ quanta/min on the average. The temperature of the tubes is maintained at 30° C.

The decomposition of the initiator employed is followed by IR at 1770 cm$^{-1}$ (caused by the carbonyl adjacent to the peroxy group) against an appropriate solvent blank. The initiators employed are p-benzoylperoxybenzoic acid tert-butylester (Ia) and prior art benzophenone peroxide. In addition, the above procedure is repeated except that methyl methacrylate is employed in place of styrene. Table IX below illustrates the relative quantum yield for the decomposition of the initiators in the recited amounts of monomers, assuming that the quantum yield for the decomposition of the perester and peroxide in the absence of any monomer is one.

TABLE IX

Relative Quantum Yield ($\phi_{rel}$) of Decomposition of Perester or Peroxide in Presence of Styrene and Methyl Methacrylate[a]

| Perester | | Peroxide | |
|---|---|---|---|
| Monomer Concentration [M] (M) | $\phi_{rel}$ | Monomer Concentration [M] (M) | $\phi_{rel}$ |
| Styrene-benzene | | Styrene-chloroform | |
| 8.73 | very low | 4.26 | 0.08 |
| 4.37 | 0.12 | 2.23 | 0.06 |
| 3.28 | 0.14 | 2.18 | 0.05 |
| 2.19 | 0.20 | | |
| 1.09 | 0.25 | | |
| Methyl methacrylate-benzene | | | |
| 4.68 | 0.80 | | |
| 2.34 | 0.88 | | |

[a] $\phi$ of perester and peroxide, in the absence of monomer, is assumed as unity; initial concentration of perester or peroxide $2 \times 10^{-2} M$ in each case.

The rates of polymerization of styrene initiated by both the peresters and peroxide are low compared to the decomposition rates of the initiators in the absence of monomer. Moreover, for the same concentration of initiators and monomer, the rate of polymerization with the perester is almost double with the peroxide, although both show near unit quantum yield for decomposition under similar conditions of irradiation in the absence of any monomer.

It has been reported that styrene, and some other vinyl monomers, act as triplet quenchers, the efficiency of quenching depending on the triplet energies of the donor and acceptor. Styrene, having a triplet energy of 62 kcal/mol, can act as a quencher for the benzophenone triplet whose triplet energy is nerely 69 kcal/mol. Styrene drastically reduces the quantum yield of decomposition for both the perester and peroxide, the quenching effect being greater with the peroxide than the perester. Lower values for the quantum yield of decomposition ($\phi_{rel}$) for the peroxide probably explains the lower rate of polymerization with it. The difference in the rates of polymerization decreases in the case of methyl methacrylate where the influence of monomer on decomposition of the initiators also is lower.

Table X below illustrates the efficiency of the radicals to initiate polymerization.

The efficiency of the radicals to initiate polymerization, f, in the absence of any appreciable amount of chain transfer, can be defined as $$f = \frac{\text{moles of polymer formed}}{\text{moles of initiator decomposed}}$$

assuming bimolecular termination by the combination of two growing chains only $$f = \frac{R_p}{\bar{p}} / k_d \phi rel$$

whereas $k_d$ = rate of decomposition of perester in mol/liter sec. in the absence of monomer (a function of light intensity).

The results in Table X show radical efficiency approaches unity at low initiator concentrations by the perester, whereas at higher concentrations of initiator, the apparent efficiency decreases considerably. At higher initiator concentrations, light absorption by the initiator also is high, so the simple kinetic treatment is not valid and, thus, the generation of radicals is no longer proportional to the initiator concentration. This will reflect in apparent lower values of initiator efficiency.

TABLE X

Radical Efficiency for the Initiation of Polymerization[a]

| Initiator concentration [I] (M × 10³) | Monomer concentration [M] (M) | $R_p \times 10^5$ (mole/liter sec) | Average degree of polymerization $\bar{p}$ | $\phi_{rel}$ | Radical efficiency f |
|---|---|---|---|---|---|
| Perester-benzene | | | | | |
| 0.31 | 3.5 | 0.65 | 320.4 | 0.14 | 0.92 |
| 0.63 | 3.5 | 0.92 | 166.7 | 0.14 | 1.21 |
| 1.15 | 3.5 | 1.29 | 155.5 | 0.14 | 1.00 |
| 2.52 | 3.5 | 1.47 | 102.8 | 0.14 | 0.79 |
| 5.03 | 3.5 | 1.72 | 85.7 | 0.14 | 0.56 |
| 8.05 | 3.5 | 1.83 | 77.2 | 0.14 | 0.41 |
| 10.0 | 2.0 | 0.95 | 48.0 | 0.25 | 0.16 |
| 10.0 | 3.5 | 1.50 | 137.2 | 0.14 | 0.15 |
| 10.0 | 5.0 | 2.08 | 219.2 | 0.12 | 0.16 |
| Perester-chloroform | | | | | |
| 0.14 | | | 4.33 | 1.32 | 186.0 |
| 1.11 | 4.33 | 1.32 | 186.0 | 0.14 | 0.89 |
| 2.28 | 4.33 | 1.83 | 130.0 | | 0.86 |
| 5.14 | 4.33 | 2.01 | 102.9 | | 0.37 |
| 9.92 | 4.33 | 2.29 | 80.5 | | 0.40 |
| Peroxide-chloroform | | | | | |
| 5.00 | 5.88 | 1.72 | 372.9 | 0.08 | 0.26 |
| 5.00 | 4.33 | 1.04 | 155.8 | 0.08 | 0.33 |

TABLE X-continued
Radical Efficiency for the Initiation of Polymerization[a]

| Initiator concentration [I] (M × 10³) | Monomer concentration [M] (M) | $R_p \times 10^5$ (mole/liter sec) | Average degree of polymerization $\bar{p}$ | $\phi_{rel}$ | Radical efficiency f |
|---|---|---|---|---|---|
| 5.00 | 3.61 | 1.07 | 159.6 | 0.08 | 0.33 |

[a]$k_d = 5.12 \times 10^{-4}$ mole/liter sec.

The polystyrene obtained from each of the above polymerizations is purified by repeated (four times) precipitation from benzene solution with methanol. Before each precipitation, the benzene solution is centrifuged to remove any insoluble material. The finely powdered polymer is filtered and dried under vacuum for two days. Known amounts of polymer are dissolved in benzene and the IR is taken (2000–1500 cm⁻¹) against benzene in 0.1-mm NaCl cells. The peaks at 1730 and 1670 cm⁻¹ for the carbonyl groups, caused by ester and benzophenones, respectively, are measured. Thermally polymerized polystyrene (control) shows no absorption in that region. The extinction coefficient of the carbonyl group at 1730 cm⁻¹ is compared with that of authenticated methyl benzoylbenzoate, which is used as a model to measure the concentration of the ester end groups in the polymer. From the concentration of the ester and the extinction resulting from the carbonyl group in the benzophenone, the absorption caused by the benzophenone that is present as the ester can be calculated. The value is subtracted from the absorption obtained at 1670 cm⁻¹ for the polymer. From the resulting absorption, the concentration of benzophenone alone is estimated from the known extinction of benzophenone at that wavelength.

The results are presented hereinbelow in Table XI.

Except for low monomer concentrations, the total number of benzophenones contained as end groups per chain is almost unity in the case of the perester and almost two in case of the peroxide initiator. Comparison of the benzophenone present as the ester with that of the benzophenone attached by a C—C bond shows that 20-30% decarboxylation occurred. Compared to the decarboxylation of the primary radicals produced from direct irradiation of ordinary peroxides (e.g., benzoyl peroxide) and peresters with a shorter wavelength of $\lambda_{max}$, this degree of decarboxylation is small. The low values of benzophenone end groups at low monomer concentration are the result of the effect of chain transfer to monomer or solvent. When the polymers used for end group analysis are from samples obtained from relatively high concentrations of sensitizers (e.g., $10 \times 10^{-3}$ M), primary radical termination could not be avoided, in which case, too, the number of benzophenones contained as end groups per chain of polymer should be one for the perester and two for the peroxide.

TABLE XI
End Group Analysis of Polystyrene

| Experiment No. | Initiator concentration [I] × 10³ (M) | Styrene concentration [M] (M) | Benzophenone as ester | Benzophenone | Total |
|---|---|---|---|---|---|
| I = perester; solvent = benzene | | | | | |
| 1 | 10 | 2 | 0.52 | 0.18 | 0.70 |
| 2 | 10 | 3.5 | 0.68 | 0.13 | 0.81 |
| 3 | 10 | 5.0 | 0.73 | 0.33 | 1.06 |

TABLE XI-continued
End Group Analysis of Polystyrene

| Experiment No. | Initiator concentration [I] × 10³ (M) | Styrene concentration [M] (M) | Benzophenone as ester | Benzophenone | Total |
|---|---|---|---|---|---|
| 4 | 10 | 7.0 | 0.81 | 0.18 | 0.99 |
| Perester-Chloroform | | | | | |
| 5 | 5.0 | 5.51 | 0.62 | 0.29 | 0.91 |
| 6 | 5.0 | 6.92 | 0.71 | 0.34 | 1.05 |
| II = Peroxide-Chloroform* | | | | | |
| 7 | 5.0 | 3.61 | 1.29 | 0.54 | 1.83 |
| 8 | 4.52 | 4.33 | 1.30 | 0.62 | 1.92 |
| 9 | 4.94 | 5.88 | 1.36 | 0.72 | 2.08 |

*The peroxide is insoluble in benzene; therefore it was compared to the perester when both are dissolved in chloroform.

EXAMPLE 6
Postcuring of Polystyrene by Additional Irradiation

Polystyrene obtained from the polymerizations 6 and 9 described in Example 5 above is irradiated at 366 nm in benzene solution containing about 2.5% by volume of secbutyl alcohol and the molecular weights of the resulting polymers are compared with their original molecular weight. The results are reported hereinbelow in Table XII. The increase is higher in the case of peroxide-initiated polymers than it is in the case of perester-initiated polymers, since the former contain an average of two benzophenone groups per chain of polymer initiated by the perester; whereas, half of that is contained in the polymer chains initiated by the perester.

TABLE XII
Effect of Irradiation of Polystyrene Containing Benzophenone End Groups in the Presence of sec-Butyl Alcohol[a]

| Exp. No. from Example 5 | Initial molecular weight ($\bar{M}_n \times 10^{-4}$) | Molecular weight after irradiation ($\bar{M}_n \times 10^{-4}$) |
|---|---|---|
| 6 | 3.20 | 4.40 |
| 9 | 3.41 | 11.20 |

[a]Solvent = benzene: contains 2.5% by volume sec-butyl alcohol; irradiation time = 3.5 hr at 366 nm.

Some additional discussion of the present invention can be found in Thijs, Gupta and Neckers, Photochemistry of Perester Initiators, J. Organic Chemistry, Vol. 44, No. 23, p. 4123–4128, November 1979, which was written by me and on my behalf, and which disclosure is incorporated herein by reference.

I claim:
1. Compound of the formula:

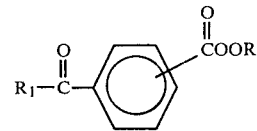

wherein R is a $C_1$–$C_{22}$ alkyl group; and $R_1$ is an organic group such that the moiety

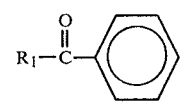

is a light absorbing chromophore group which produces an excited state by light absorption and is selected from the group consisting of $C_1-C_{22}$ alkyl groups, $C_3-C_{22}$ cycloalkyl groups, $C_6-C_{22}$ aryl groups, $C_7-C_{22}$ aralkyl groups, $C_7-C_{22}$ alkaryl groups, $C_1-C_{22}$ alkoxy substituted aryl groups and morpholinyl, piperidyl, thiophenyl and furanyl heterocyclic groups.

2. The compound of claim 1 wherein R contains 1-12 carbon atoms.

3. The compound of claim 1 wherein R contains a tertiary carbon atom connected to the oxygen atom.

4. The compound of claim 1 wherein R is tert.-butyl.

5. The compound of claim 1 wherein $R_1$ is $C_1-C_{22}$ alkyl.

6. The compound of claim 1 wherein $R_1$ is phenyl or $C_1-C_{22}$ alkyl-substituted phenyl or $C_1-C_{22}$ alkoxy-substituted phenyl.

7. The compound of claim 1 or 4 wherein $R_1$ is phenyl.

8. The compound of claim 1 or 4 wherein $R_1$ is mesityl.

9. The compound of claim 1 or 4 wherein $R_1$ is methoxy phenyl.

10. The compound of claim 1 or 4 wherein $R_1$ is propyl.

* * * * *